(12) United States Patent
Gregorich et al.

(10) Patent No.: US 8,343,211 B2
(45) Date of Patent: Jan. 1, 2013

(54) CONNECTORS FOR BIFURCATED STENT

(75) Inventors: Daniel Gregorich, St. Louis Park, MN (US); Michael P. Meyer, Richfield, MN (US); Richard C. Tooley, Crystal, MN (US); Shawn Sorenson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1335 days.

(21) Appl. No.: 11/300,033

(22) Filed: Dec. 14, 2005

(65) Prior Publication Data

US 2007/0135903 A1 Jun. 14, 2007

(51) Int. Cl.
*A61F 2/06* (2006.01)
(52) U.S. Cl. ...................................... 623/1.35
(58) Field of Classification Search ............... 623/1.15, 623/1.35, 1.11, 1.34; 604/523, 96.01
See application file for complete search history.

(56) References Cited

U.S. PATENT DOCUMENTS

| 1,596,754 | A | 8/1926 | Moschelle |
| 1,861,769 | A | 6/1932 | Wappler |
| 2,845,959 | A | 8/1958 | Sidebotham |
| 3,872,893 | A | 3/1975 | Roberts ........................ 138/121 |
| 4,309,994 | A | 1/1982 | Grunwald ................. 128/214 R |
| 4,410,476 | A | 10/1983 | Redding et al. .............. 264/173 |
| 4,413,989 | A | 11/1983 | Schjeldahl et al. ............. 604/96 |
| 4,421,810 | A | 12/1983 | Rasmussen ................... 428/109 |
| 4,454,887 | A | 6/1984 | Kruger ........................... 128/772 |
| 4,552,554 | A | 11/1985 | Gould et al. .................... 604/51 |
| 4,681,570 | A | 7/1987 | Dalton ........................... 604/282 |
| 4,689,174 | A | 8/1987 | Lupke ............................ 156/470 |
| 4,730,616 | A | 3/1988 | Frisbie et al. .............. 128/348.1 |
| 4,769,005 | A | 9/1988 | Ginsburg et al. ............... 604/53 |
| 4,774,949 | A | 10/1988 | Fogarty .......................... 128/348 |
| 4,896,670 | A | 1/1990 | Crittenden .................... 606/194 |
| 4,900,314 | A | 2/1990 | Quackenbush ............... 604/282 |
| 4,905,667 | A | 3/1990 | Foerster et al. ..................... 128/4 |
| 4,957,508 | A | 9/1990 | Kaneko et al. .................. 632/12 |
| 4,983,166 | A | 1/1991 | Yamawaki ...................... 604/96 |
| 4,994,071 | A | 2/1991 | MacGregor ................... 606/194 |
| 5,054,501 | A | 10/1991 | Chuttani et al. .............. 128/772 |

(Continued)

FOREIGN PATENT DOCUMENTS

CA 2220864 7/1999

(Continued)

OTHER PUBLICATIONS

TRIO™ 14 PTCA Catheter, Re-engineering Over the Wire Balloon Technology, Company Brochure Copyright 1994.

(Continued)

*Primary Examiner* — Ryan Severson
*Assistant Examiner* — Sarah Simpson
(74) *Attorney, Agent, or Firm* — Vidas, Arrett & Steinkraus

(57) ABSTRACT

A stent assembly comprises a second stent body and a substantially tubular first stent body defining a first lumen and containing a side branch opening. In an undeployed state, the second stent body is at least partially comprised of rings having peaks and valleys at least some of the valleys of adjacent rings being interconnected by bridges. In an expanded state, the rings of the second stent body define a second lumen opening in fluid communication with the first lumen. The second lumen has superior body vessel coverage and is flexible enough to form an oblique angle relative to the longitudinal axis of the first stent body.

19 Claims, 3 Drawing Sheets

U.S. PATENT DOCUMENTS

| | | | |
|---|---|---|---|
| 5,122,125 A | 6/1992 | Deuss | 604/282 |
| 5,147,317 A | 9/1992 | Shank et al. | 604/164 |
| 5,156,620 A | 10/1992 | Pigott | 623/1 |
| 5,217,440 A | 6/1993 | Frassica | 604/282 |
| 5,219,355 A | 6/1993 | Parodi et al. | 606/191 |
| 5,244,619 A | 9/1993 | Burnham | 264/173 |
| 5,320,605 A | 6/1994 | Sahota | 604/101 |
| 5,337,733 A | 8/1994 | Bauerfeind et al. | 128/4 |
| 5,342,387 A | 8/1994 | Summers | 606/198 |
| 5,350,395 A | 9/1994 | Yock | 606/194 |
| 5,387,235 A | 2/1995 | Chuter | 623/1 |
| 5,404,887 A | 4/1995 | Prather | 128/772 |
| 5,417,208 A | 5/1995 | Winkler | 128/642 |
| 5,443,497 A | 8/1995 | Venbrux | 623/1 |
| 5,445,624 A | 8/1995 | Jimenez | 604/280 |
| 5,456,712 A | 10/1995 | Maginot | 623/1 |
| 5,458,605 A | 10/1995 | Klemm | 606/108 |
| 5,476,471 A | 12/1995 | Shifrin et al. | 606/151 |
| 5,487,730 A | 1/1996 | Marcadis et al. | 604/96 |
| 5,489,271 A | 2/1996 | Andersen | 604/102 |
| 5,496,292 A | 3/1996 | Burnham | 604/282 |
| 5,575,771 A | 11/1996 | Walinsky | 604/96 |
| 5,591,228 A | 1/1997 | Edoga | 623/1 |
| 5,599,300 A | 2/1997 | Weaver et al. | 604/54 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,639,278 A | 6/1997 | Dereume et al. | 623/1 |
| 5,669,924 A | 9/1997 | Shaknovich | 606/108 |
| 5,669,932 A | 9/1997 | Fishell et al. | 606/198 |
| 5,672,153 A | 9/1997 | Lax et al. | 604/22 |
| 5,676,697 A | 10/1997 | McDonald | 623/1 |
| 5,683,450 A | 11/1997 | Goicoechea et al. | 623/1 |
| 5,693,086 A | 12/1997 | Goicoechea et al. | 623/1 |
| 5,695,516 A * | 12/1997 | Fischell et al. | 606/194 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,770 A | 5/1998 | Ravenscroft | 623/1 |
| 5,755,771 A | 5/1998 | Penn et al. | 623/1 |
| 5,755,772 A | 5/1998 | Evans et al. | 623/1 |
| 5,755,773 A | 5/1998 | Evans et al. | 623/1 |
| 5,755,778 A | 5/1998 | Kleshinski | 623/1 |
| 5,776,101 A | 7/1998 | Goy | 604/104 |
| 5,782,906 A | 7/1998 | Marshall et al. | 604/194 |
| 5,800,508 A | 9/1998 | Goicoechea et al. | 623/1 |
| 5,800,520 A | 9/1998 | Fogarty et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,853,419 A * | 12/1998 | Imran | 623/1.15 |
| 5,855,600 A | 1/1999 | Alt | 623/1 |
| 5,868,777 A | 2/1999 | Lam | 606/194 |
| 5,893,887 A | 4/1999 | Jayaraman | 623/1 |
| 5,906,640 A | 5/1999 | Penn et al. | 623/1 |
| 5,916,263 A | 6/1999 | Goicoechea et al. | 623/1 |
| 5,921,995 A | 7/1999 | Kleshinski | 606/153 |
| 5,938,696 A | 8/1999 | Goicoechea et al. | 623/1 |
| 5,961,490 A | 10/1999 | Adams | 604/96 |
| 5,961,548 A | 10/1999 | Shmulewitz | 623/1 |
| 5,968,089 A | 10/1999 | Krajicek | 623/1 |
| 5,972,017 A | 10/1999 | Berg et al. | 606/198 |
| 5,984,955 A | 11/1999 | Wisselink | 623/1 |
| 5,993,481 A | 11/1999 | Marcade et al. | 623/1 |
| 6,013,054 A | 1/2000 | Jiun Yan | 604/96 |
| 6,013,091 A | 1/2000 | Ley et al. | 83/150 |
| 6,016,810 A | 1/2000 | Ravenscroft | 128/898 |
| 6,017,324 A | 1/2000 | Tu et al. | 604/96 |
| 6,017,363 A | 1/2000 | Jojeibane | 623/1 |
| 6,030,414 A | 2/2000 | Taheri | 623/1 |
| 6,033,433 A | 3/2000 | Ehr et al. | 623/1 |
| 6,033,434 A | 3/2000 | Borghi | 623/1 |
| 6,033,435 A | 3/2000 | Penn et al. | 623/1 |
| 6,039,758 A | 3/2000 | Quiachon et al. | 623/1 |
| 6,045,557 A | 4/2000 | White et al. | 606/108 |
| 6,048,360 A | 4/2000 | Khosravi et al. | 623/1 |
| 6,048,361 A | 4/2000 | Von Oepen | 623/1 |
| 6,051,020 A | 4/2000 | Goicoechea et al. | 623/1 |
| 6,056,722 A | 5/2000 | Jayaraman | 604/102 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,071,298 A | 6/2000 | Lashinski et al. | 606/198 |
| 6,086,611 A | 7/2000 | Duffy et al. | 623/1 |
| 6,090,133 A | 7/2000 | Richter et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,099,558 A | 8/2000 | White | 623/1.16 |
| 6,099,560 A | 8/2000 | Penn et al. | 623/1.35 |
| 6,102,938 A | 8/2000 | Evans et al. | 623/1 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,129,738 A | 10/2000 | Lashinski et al. | 606/194 |
| 6,129,754 A | 10/2000 | Kanesaka et al. | 623/1 |
| 6,132,459 A | 10/2000 | Piplani et al. | 623/1.13 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 623/1.11 |
| 6,165,195 A | 12/2000 | Wilson et al. | 606/194 |
| 6,165,213 A | 12/2000 | Goccoechea et al. | 623/1.34 |
| 6,168,621 B1 | 1/2001 | Vrba | 623/1.2 |
| 6,183,509 B1 | 2/2001 | Dibie | 623/1.35 |
| 6,197,046 B1 | 3/2001 | Piplani et al. | 623/1.11 |
| 6,197,049 B1 | 3/2001 | Shaolian et al. | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1 |
| 6,210,431 B1 | 4/2001 | Power | 623/1.11 |
| 6,210,433 B1 | 4/2001 | Larre | 623/1.15 |
| 6,217,527 B1 | 4/2001 | Selmon et al. | 600/285 |
| 6,221,080 B1 | 4/2001 | Power | 606/108 |
| 6,221,090 B1 | 4/2001 | Wilson | 606/194 |
| 6,221,098 B1 | 4/2001 | Wilson et al. | 623/1.11 |
| 6,231,563 B1 | 5/2001 | White et al. | 604/523 |
| 6,231,598 B1 | 5/2001 | Berry et al. | 623/1.15 |
| 6,238,430 B1 | 5/2001 | Klumb et al. | 623/1.11 |
| 6,248,122 B1 | 6/2001 | Klumb et al. | 606/194 |
| 6,251,133 B1 | 6/2001 | Richter et al. | 623/1.16 |
| 6,254,593 B1 | 7/2001 | Wilson | 606/1.11 |
| 6,258,073 B1 | 7/2001 | Mauch | 604/284 |
| 6,258,115 B1 | 7/2001 | Dubrul | 606/200 |
| 6,258,116 B1 | 7/2001 | Hojeibane | 623/1.16 |
| 6,261,273 B1 | 7/2001 | Ruiz | 604/284 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,273,909 B1 | 8/2001 | Kugler et al. | 623/1.13 |
| 6,283,991 B1 * | 9/2001 | Cox et al. | 623/1.13 |
| 6,287,277 B1 | 9/2001 | Yan | 604/96.01 |
| 6,290,673 B1 | 9/2001 | Shanley | 604/102 |
| 6,293,968 B1 | 9/2001 | Taheri | 623/1.15 |
| 6,302,906 B1 | 10/2001 | Goicoechea et al. | 623/1.11 |
| 6,302,908 B1 | 10/2001 | Parodi | 623/1.31 |
| 6,306,164 B1 | 10/2001 | Kujawski | 623/1.25 |
| 6,312,461 B1 | 11/2001 | Unsworth et al. | 623/1.19 |
| 6,319,278 B1 | 11/2001 | Quinn et al. | 623/1.13 |
| 6,322,587 B1 | 11/2001 | Quiachon et al. | 623/1.23 |
| 6,325,819 B1 | 12/2001 | Pavcnik et al. | 623/1.11 |
| 6,325,822 B1 | 12/2001 | Chouinard et al. | 623/1.15 |
| 6,325,826 B1 | 12/2001 | Vardi et al. | 623/1.35 |
| 6,334,864 B1 | 1/2002 | Amplatz et al. | 606/200 |
| 6,334,870 B1 | 1/2002 | Ehr | 623/1.16 |

| | | | | | | |
|---|---|---|---|---|---|---|
| 6,346,089 B1 | 2/2002 | Dibie | 623/1.15 | 2002/0173835 A1 | 11/2002 | Bourang et al. | 623/1.11 |
| 6,355,060 B1 | 3/2002 | Lenker et al. | 623/1.34 | 2002/0173840 A1 | 11/2002 | Brucker et al. | 623/1.16 |
| 6,361,544 B1 | 3/2002 | Wilson et al. | 606/194 | 2002/0183763 A1 | 12/2002 | Callol et al. | 606/108 |
| 6,361,555 B1 | 3/2002 | Wilson | 623/1.11 | 2002/0193872 A1 | 12/2002 | Trout, III et al. | 623/1.34 |
| 6,383,213 B2 | 5/2002 | Wilson et al. | 623/1.11 | 2002/0193873 A1 | 12/2002 | Brucker | 623/1.11 |
| 6,387,120 B2 | 5/2002 | Wilson et al. | 623/1.11 | 2003/0009209 A1 | 1/2003 | Hojeibane | 623/1.11 |
| 6,395,018 B1 | 5/2002 | Castaneda | 623/1.13 | 2003/0028233 A1 | 2/2003 | Vardi et al. | 623/1.11 |
| 6,436,104 B2 | 8/2002 | Hojeibane | 606/108 | 2003/0050688 A1 | 3/2003 | Fischell et al. | 623/1.15 |
| 6,436,134 B2 | 8/2002 | Richter et al. | 623/1.15 | 2003/0055378 A1 | 3/2003 | Wang et al. | 604/103.07 |
| 6,468,301 B1 | 10/2002 | Amplatz et al. | 623/1.13 | 2003/0055483 A1 | 3/2003 | Gumm | 623/1.11 |
| 6,508,836 B2 | 1/2003 | Wilson et al. | 623/1.35 | 2003/0074047 A1 | 4/2003 | Richter | 623/1.11 |
| 6,517,558 B2 | 2/2003 | Gittings et al. | 606/153 | 2003/0093109 A1 | 5/2003 | Mauch | 606/194 |
| 6,520,988 B1 | 2/2003 | Colombo et al. | 623/1.35 | 2003/0097169 A1 | 5/2003 | Brucker | 623/1.11 |
| 6,537,284 B1 | 3/2003 | Inoue | 606/108 | 2003/0114912 A1 | 6/2003 | Sequin et al. | 623/1.11 |
| 6,540,779 B2 | 4/2003 | Richter et al. | 623/1.35 | 2003/0125791 A1 | 7/2003 | Sequin et al. | 623/1.11 |
| 6,579,309 B1 | 6/2003 | Loos | 623/1.16 | 2003/0125802 A1 | 7/2003 | Callol et al. | 623/1.35 |
| 6,579,312 B2 | 6/2003 | Wilson et al. | 623/1.35 | 2003/0135259 A1 | 7/2003 | Simso | 623/1.12 |
| 6,582,394 B1 | 6/2003 | Reiss | 604/96 | 2003/0181923 A1 | 9/2003 | Vardi | 606/108 |
| 6,596,020 B2 | 7/2003 | Vardi et al. | 623/1.11 | 2003/0195606 A1 | 10/2003 | Davidson et al. | 623/1.11 |
| 6,599,315 B2 | 7/2003 | Wilson | 623/1.11 | 2004/0006381 A1 | 1/2004 | Sequin et al. | 623/1.12 |
| 6,599,316 B2 | 7/2003 | Vardi et al. | 623/1.15 | 2004/0015227 A1 | 1/2004 | Vardi et al. | 623/1.16 |
| 6,645,242 B1 | 11/2003 | Quinn | 623/1.16 | 2004/0044396 A1 | 3/2004 | Clerc et al. | 623/1.13 |
| 6,689,156 B1 | 2/2004 | Davidson et al. | 623/1.11 | 2004/0059406 A1 | 3/2004 | Cully et al. | 623/1.11 |
| 6,692,483 B2 | 2/2004 | Vardi et al. | 604/529 | 2004/0088007 A1 | 5/2004 | Eidenschink | 607/1 |
| 6,695,877 B2 | 2/2004 | Brucker et al. | 623/1.16 | 2004/0117003 A1 | 6/2004 | Ouriel et al. | 623/1.35 |
| 6,706,062 B2 | 3/2004 | Vardi et al. | 623/1.15 | 2004/0133268 A1 | 7/2004 | Davidson et al. | 623/1.35 |
| 6,749,628 B1 | 6/2004 | Callol et al. | 623/1.15 | 2004/0138732 A1 | 7/2004 | Suhr et al. | 623/1.11 |
| 6,776,793 B2 | 8/2004 | Brown et al. | 623/1.15 | 2004/0138737 A1* | 7/2004 | Davidson et al. | 623/1.35 |
| 6,811,566 B1 | 11/2004 | Penn et al. | 623/1.15 | 2004/0148006 A1 | 7/2004 | Davidson et al. | 623/1.11 |
| 6,835,203 B1 | 12/2004 | Vardi | 623/1.16 | 2004/0172121 A1 | 9/2004 | Eidenschink et al. | 623/1.11 |
| 6,858,038 B2 | 2/2005 | Heuser | 623/1.35 | 2004/0186560 A1 | 9/2004 | Alt | 623/1.35 |
| 6,884,258 B2 | 4/2005 | Vardi et al. | 623/1.11 | 2004/0225345 A1 | 11/2004 | Fischell et al. | 623/1.11 |
| 6,896,699 B2 | 5/2005 | Wilson et al. | 623/1.35 | 2004/0267352 A1 | 12/2004 | Davidson | 623/1.11 |
| 6,932,837 B2 | 8/2005 | Amplatz et al. | 623/1.15 | 2005/0004656 A1 | 1/2005 | Das | 623/1.16 |
| 6,955,687 B2 | 10/2005 | Richter et al. | 623/1.35 | 2005/0010278 A1 | 1/2005 | Vardi et al. | 623/1.35 |
| 6,955,688 B2 | 10/2005 | Wilson et al. | 623/1.35 | 2005/0015108 A1 | 1/2005 | Williams et al. | 606/194 |
| 6,962,602 B2 | 11/2005 | Vardi et al. | 623/1.11 | 2005/0015135 A1 | 1/2005 | Shanley | 623/1.11 |
| 7,018,400 B2 | 3/2006 | Lashinski et al. | 623/1.11 | 2005/0060027 A1 | 3/2005 | Khenansho et al. | 623/1.35 |
| 7,056,323 B2 | 6/2006 | Mareiro et al. | 606/108 | 2005/0096726 A1 | 5/2005 | Sequin et al. | 623/1.12 |
| 7,060,091 B2 | 6/2006 | Killion et al. | 623/1.15 | 2005/0102021 A1 | 5/2005 | Osborne | 623/1.13 |
| 7,341,598 B2* | 3/2008 | Davidson et al. | 623/1.35 | 2005/0102023 A1* | 5/2005 | Yadin et al. | 623/1.15 |
| 2001/0002443 A1 | 5/2001 | Parodi | | 2005/0113909 A1* | 5/2005 | Shannon et al. | 623/1.46 |
| 2001/0002927 A1 | 6/2001 | Detampel | | 2005/0119731 A1 | 6/2005 | Brucker et al. | 623/1.35 |
| 2001/0002943 A1 | 6/2001 | Nagayama et al. | | 2005/0125051 A1 | 6/2005 | Eidenschink et al. | 623/1.12 |
| 2001/0003161 A1 | 6/2001 | Vardi et al. | | 2005/0125076 A1 | 6/2005 | Ginn | 623/23.65 |
| 2001/0004705 A1 | 6/2001 | Killion et al. | | 2005/0131526 A1 | 6/2005 | Wong | |
| 2001/0004706 A1 | 6/2001 | Hojeibane | | 2005/0149161 A1 | 7/2005 | Eidenschink et al. | 623/1.11 |
| 2001/0004707 A1 | 6/2001 | Dereume et al. | | 2005/0154442 A1 | 7/2005 | Eidenschink et al. | 623/1.11 |
| 2001/0004823 A1 | 6/2001 | Cronin et al. | | 2005/0154444 A1 | 7/2005 | Quadri et al. | 623/1.23 |
| 2001/0007954 A1 | 7/2001 | Shaolian et al. | | 2005/0183259 A1 | 8/2005 | Eidenschink et al. | 29/508 |
| 2001/0012927 A1 | 8/2001 | Mauch | 604/284 | 2005/0209673 A1 | 9/2005 | Shaked | 623/1.11 |
| 2001/0016766 A1 | 8/2001 | Vardi et al. | | 2005/0228483 A1 | 10/2005 | Kaplan | 623/1.11 |
| 2001/0016767 A1 | 8/2001 | Wilson et al. | | 2006/0036135 A1 | 2/2006 | Yadin et al. | 623/1.35 |
| 2001/0016768 A1 | 8/2001 | Wilson et al. | | 2006/0041303 A1 | 2/2006 | Israel | 623/1.11 |
| 2001/0020173 A1 | 9/2001 | Klumb et al. | | 2006/0079956 A1 | 4/2006 | Eigler et al. | 623/1.35 |
| 2001/0020184 A1 | 9/2001 | Dehdashtian et al. | | 2006/0173528 A1 | 8/2006 | Feld et al. | 623/1.15 |
| 2001/0025195 A1 | 9/2001 | Shaolian et al. | | 2007/0073376 A1 | 3/2007 | Krolik et al. | 623/1.11 |
| 2001/0027291 A1 | 10/2001 | Shanley | | 2007/0208411 A1* | 9/2007 | Meyer et al. | 623/1.15 |
| 2001/0027338 A1 | 10/2001 | Greenberg | 623/1.13 | 2007/0276464 A1* | 11/2007 | Valencia et al. | 623/1.15 |
| 2001/0029396 A1 | 10/2001 | Wilson et al. | | 2008/0065197 A1* | 3/2008 | Meyer et al. | 623/1.16 |
| 2001/0037116 A1 | 11/2001 | Wilson et al. | 606/108 | 2008/0086200 A1* | 4/2008 | Macha | 623/1.42 |
| 2001/0037138 A1 | 11/2001 | Wilson et al. | 623/1.11 | | | | |
| 2001/0039448 A1 | 11/2001 | Dibie | 623/1.16 | | | | |
| 2001/0047199 A1* | 11/2001 | Wijay | 623/1.15 | | | | |
| 2001/0049552 A1 | 12/2001 | Richter et al. | 623/1.15 | | | | |
| 2001/0056297 A1 | 12/2001 | Hojeibane | 623/1.16 | | | | |
| 2002/0013618 A1 | 1/2002 | Marotta et al. | 623/1.15 | | | | |
| 2002/0013619 A1 | 1/2002 | Shanley | 623/1.15 | | | | |
| 2002/0022874 A1 | 2/2002 | Wilson | 623/1.11 | | | | |
| 2002/0026232 A1 | 2/2002 | Marotta et al. | 623/1.16 | | | | |
| 2002/0035392 A1 | 3/2002 | Wilson | 623/1.11 | | | | |
| 2002/0042650 A1 | 4/2002 | Vardi et al. | 623/1.35 | | | | |
| 2002/0052648 A1 | 5/2002 | McGuckin, Jr. et al. | 623/1.35 | | | | |
| 2002/0072790 A1 | 6/2002 | McGuckin, Jr. et al. | 623/1.12 | | | | |
| 2002/0111675 A1 | 8/2002 | Wilson | 715/530 | | | | |
| 2002/0123791 A1* | 9/2002 | Harrison | 623/1.15 | | | | |
| 2002/0156516 A1 | 10/2002 | Vardi et al. | 623/1.11 | | | | |
| 2002/0156517 A1 | 10/2002 | Perouse | 623/1.11 | | | | |
| 2002/0165604 A1 | 11/2002 | Shanley | 623/1.15 | | | | |

FOREIGN PATENT DOCUMENTS

| | | |
|---|---|---|
| DE | 9014845 | 2/1991 |
| DE | 29701883 | 3/1997 |
| DE | 29701758 | 5/1997 |
| EP | 0479730 | 10/1991 |
| EP | 0686379 | 12/1995 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0647148 | 12/1998 |
| EP | 0880949 | 12/1998 |
| EP | 0891751 | 1/1999 |
| EP | 0895759 | 2/1999 |
| EP | 0897700 | 2/1999 |
| EP | 0904745 | 3/1999 |

| | | |
|---|---|---|
| EP | 0937442 | 8/1999 |
| EP | 0347023 | 12/1999 |
| EP | 1031328 | 8/2000 |
| EP | 1031329 | 8/2000 |
| EP | 1031330 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0684022 | 2/2004 |
| EP | 1157674 | 7/2005 |
| EP | 1070513 | 6/2006 |
| FR | 2678508 | 7/1991 |
| FR | 2740346 | 10/1995 |
| FR | 2756173 | 11/1996 |
| FR | 2760351 | 3/1997 |
| GB | 2337002 | 5/1998 |
| WO | 88/06026 | 8/1988 |
| WO | 92/19308 | 11/1992 |
| WO | 9510442 | 4/1995 |
| WO | 9521592 | 8/1995 |
| WO | 96/29955 | 10/1996 |
| WO | 9634580 | 11/1996 |
| WO | 9641592 | 12/1996 |
| WO | 9707752 | 3/1997 |
| WO | 9715346 | 5/1997 |
| WO | 9716217 | 5/1997 |
| WO | 97/26936 | 7/1997 |
| WO | 9741803 | 11/1997 |
| WO | 97/45073 | 12/1997 |
| WO | 9746174 | 12/1997 |
| WO | 9819628 | 5/1998 |
| WO | 9836709 | 8/1998 |
| WO | 9837833 | 9/1998 |
| WO | 9847446 | 10/1998 |
| WO | 9847447 | 10/1998 |
| WO | 9848879 | 11/1998 |
| WO | 9853759 | 12/1998 |
| WO | 9903426 | 1/1999 |
| WO | 9903462 | 1/1999 |
| WO | 9904726 | 2/1999 |
| WO | 9913808 | 3/1999 |
| WO | 99/15103 | 4/1999 |
| WO | 9915108 | 4/1999 |
| WO | 9915109 | 4/1999 |
| WO | 9924104 | 5/1999 |
| WO | 9934749 | 7/1999 |
| WO | 9936002 | 7/1999 |
| WO | 9936015 | 7/1999 |
| WO | 9944539 | 9/1999 |
| WO | 9956661 | 11/1999 |
| WO | 9965419 | 12/1999 |
| WO | 0007523 | 2/2000 |
| WO | 0010485 | 3/2000 |
| WO | 0010489 | 3/2000 |
| WO | 0013613 | 3/2000 |
| WO | 0016719 | 3/2000 |
| WO | 0027307 | 5/2000 |
| WO | 0027463 | 5/2000 |
| WO | 0028922 | 5/2000 |
| WO | 0032266 | 6/2000 |
| WO | 0044307 | 8/2000 |
| WO | 0044309 | 8/2000 |
| WO | 0047134 | 8/2000 |
| WO | 0048531 | 8/2000 |
| WO | 0049951 | 8/2000 |
| WO | 0051523 | 9/2000 |
| WO | 0057813 | 10/2000 |
| WO | 00/71054 | 11/2000 |
| WO | 0067673 | 11/2000 |
| WO | 0071055 | 11/2000 |
| WO | 0074595 | 12/2000 |
| WO | 0121095 | 3/2001 |
| WO | 0121109 | 3/2001 |
| WO | 0121244 | 5/2001 |
| WO | 0130433 | 5/2001 |
| WO | 0135715 | 5/2001 |
| WO | 0135863 | 5/2001 |
| WO | 0139697 | 6/2001 |
| WO | 0139699 | 6/2001 |
| WO | 0141677 | 6/2001 |
| WO | 0143665 | 6/2001 |
| WO | 0143809 | 6/2001 |
| WO | 0145594 | 6/2001 |
| WO | 0145785 | 6/2001 |
| WO | 0149342 | 7/2001 |
| WO | 0154621 | 8/2001 |
| WO | 0154622 | 8/2001 |
| WO | 0158385 | 8/2001 |
| WO | 0160284 | 8/2001 |
| WO | 0170294 | 9/2001 |
| WO | 0170299 | 9/2001 |
| WO | 0174273 | 10/2001 |
| WO | 0189409 | 11/2001 |
| WO | 02/00138 | 1/2002 |
| WO | 02/053066 A1 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2004/026180 A2 | 4/2004 |
| WO | 2005/009295 | 2/2005 |
| WO | 2005/014077 | 2/2005 |
| WO | 2006/028925 | 3/2006 |

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, "Kissing" Stent for Bifurcational Coronary Lesion, *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions", *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/325,996, filed Jun. 4, 1999, Vardi et al.
U.S. Appl. No. 09/614,472, filed Jul. 11, 2000, Davidson et al.
U.S. Appl. No. 09/663,111, filed Sep. 15, 2000, Davidson et al.

* cited by examiner

CONNECTORS FOR BIFURCATED STENT

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be implanted to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

At least one possible embodiment is directed to a stent comprising a tubular body having a sidewall with a plurality of openings therethrough. A portion of the sidewall has a plurality of rings which are concentric and interconnected, including a first ring and a second ring. Both rings have peaks and valleys. A first connector extending from a valley of the first ring to the valley of the second ring connects the rings.

At least one possible embodiment is directed to a stent wherein the first and second rings are connected by a plurality of connectors, the connectors extending from one valleys of the first ring to valleys of the second ring.

At least one possible embodiment is directed to a stent wherein each of the concentric rings has a plurality of peaks and valleys, each two adjacent concentric rings connected by at least one connector which extends from a valley of one of the two adjacent rings to a valley of the other of the two adjacent rings.

At least one possible embodiment is directed to a stent wherein each of the concentric rings has a plurality of peaks and valleys, each two adjacent concentric rings connected by a plurality of connectors which extend from valleys of one of the two adjacent rings to valleys of the other of the two adjacent rings.

At least one possible embodiment is directed to a stent in which the peaks and valleys of the concentric rings are out of phase with each other.

At least one possible embodiment is directed to a stent in which at least one connector is more rigid than at least one ring.

At least one possible embodiment is directed to a stent in which at least one ring is more rigid than at least one connector.

At least one possible embodiment is directed to a stent in which at least one connector and at least one concentric ring are constructed out of different materials.

At least one possible embodiment is directed to a stent in which the connectors are connected to every other valley of at least one ring.

At least one possible embodiment is directed to a bifurcated stent having a tubular sidewall, the sidewall including an expandable sidebranch portion, the expandable sidebranch portion having a plurality of rings which are concentric and interconnected, including a first ring and a second ring. Both rings have peaks and valleys. A first connector extending from a valley of the first ring to the valley of the second ring connects the rings.

At least one possible embodiment is directed to a bifurcated stent in which the first and second rings are connected by a plurality of connectors, the connectors extending from one valleys of the first ring to valleys of the second ring.

At least one possible embodiment is directed to a bifurcated stent in which the first ring defines the outermost end of the expandable sidebranch portion.

At least one possible embodiment is directed to a bifurcated stent in which the peaks and valleys of the concentric rings are out of phase with each other.

At least one possible embodiment is directed to a bifurcated stent in which at least one connector is more rigid than at least one ring.

At least one possible embodiment is directed to a bifurcated stent in which at least one ring is more rigid than at least one connector.

At least one possible embodiment is directed to a bifurcated stent in which at least one connector and at least one concentric ring are constructed out of different materials.

At least one possible embodiment is directed to a bifurcated stent in which the connectors are connected to every other valley of at least one ring.

At least one possible embodiment is directed to a bifurcated stent being expandable from an unexpanded state to an expanded state, wherein in the unexpanded state the stent has a diameter less than that of the diameter in the expanded state. The bifurcated stent comprises: a substantially tubular primary body defining a primary circumferential plane, a primary outer surface, a primary lumen and having a primary longitudinal axis extending therethrough and has a side opening and a side branch assembly engaged to the primary body opposite the side opening. The side branch assembly comprises at least two ring members. In the unexpanded state the at least two ring members are positioned substantially within the primary circumferential plane. In the expanded state at least one ring member is positioned external to the first circumferential plane and the at least two ring members define a secondary circumferential plane, a secondary lumen, and having a secondary longitudinal axis extending therethrough. The secondary lumen is in fluid communication with the primary lumen and the secondary longitudinal axis forms an oblique angle with the primary longitudinal axis. The ring members are interconnected by connectors and comprising a plurality of peaks and valleys, at least one of the connectors connecting the valley of one ring member to the valley of another ring member.

At least one possible embodiment is directed to a bifurcated stent in which one half of all the valleys of at least one ring members are connected to one half of the ring members of at least one other ring member.

These and other embodiments which characterize the invention are pointed out with particularity in the claims annexed hereto and forming a part hereof.

However, for further understanding of the invention, its advantages and objectives obtained by its use, reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
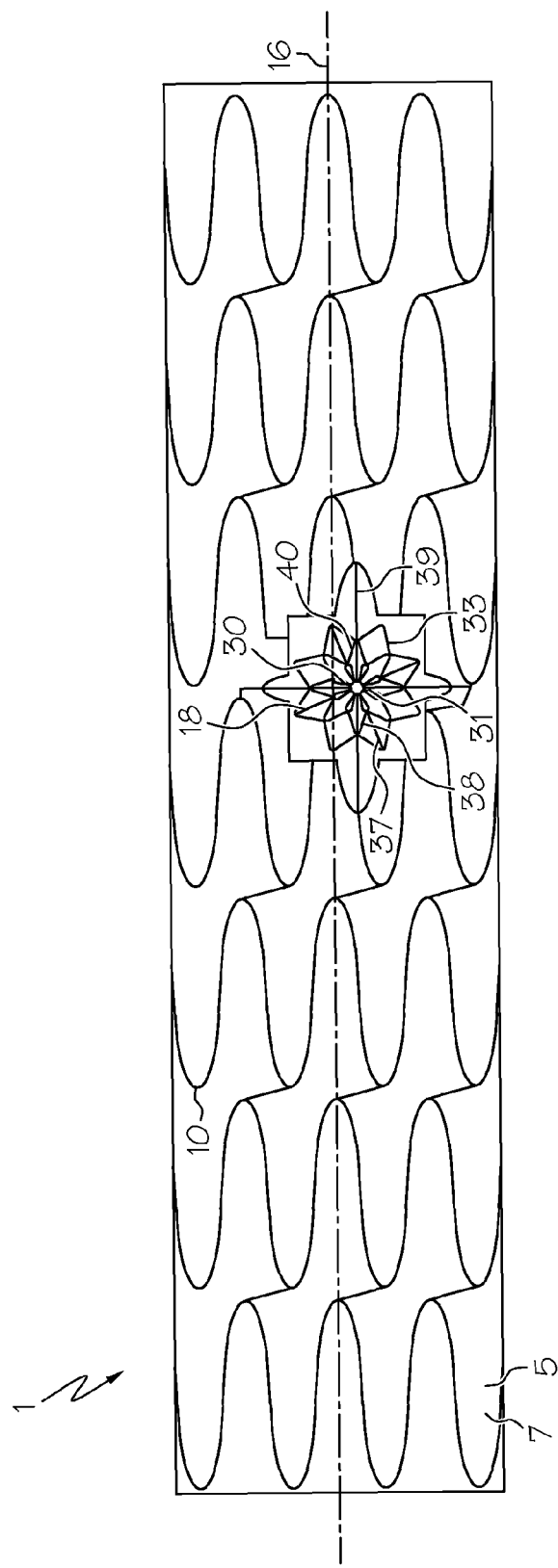
FIG. 1 is a view of an unexpanded bifurcated stent having a side branch assembly with bridged rings.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Referring now to FIG. 1 there is shown a tubular body which is an unexpanded bifurcated stent 1 extending along a first longitudinal axis 16 having a first stent body 10 with at least one side opening 18 along its sidewall. Although this illustration shows a first stent body 10 having a plurality of struts 5 forming columns 7, the invention encompasses all stent structures currently known in the art. In the expanded state, the first stent body will define a first fluid lumen 14.

First stent body 10 can be constructed from any suitable biocompatible material including but not limited to polymers, stainless steel, platinum, gold, cobalt, chromium, niobium etc. It can also be constructed out of one or more combinations and/or alloys of these materials.

Figure 2:
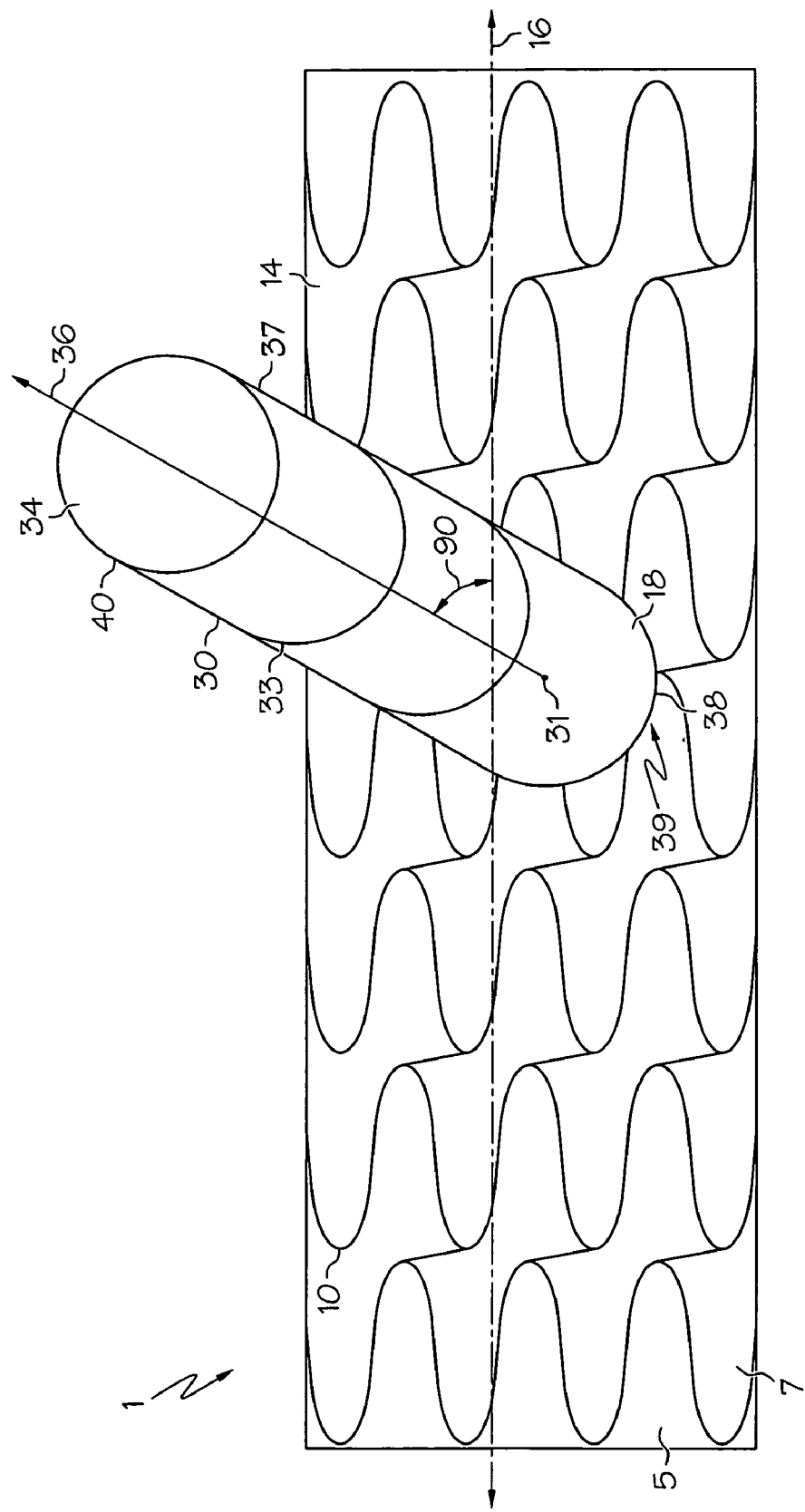
FIG. 2 is a view of an expanded bifurcated stent having a side branch assembly with bridged rings.

An improved side branch assembly 30 is connected to first stent body 10 adjacent to the side opening 18. As illustrated in FIG. 2, when the stent is in its expanded state, the side branch assembly 30 will define a second fluid lumen 34 in fluid communication with the first fluid lumen 14 with a second longitudinal axis 36 extending therethrough. The second longitudinal axis 36 can be oriented at an angle 90 with respect to the longitudinal axis 16 of the first stent body 10. The region of the side branch assembly 30 that is generally connected to the first stent body 10 by connectors 39 in the expanded state comprises an end of the second fluid lumen 34 and is referred to as the "ostium" 38. The opposite end of the expanded second fluid lumen 34 is the outermost end 40. For purposes of this application and in particular when describing the drawings, when discussing a set of items, the item described as "ostial" is the item of the set closest to the ostium and the item described as "outermost" is the item of the set furthest away from the ostium.

The side branch assembly 30 of FIGS. 1 and 2 comprises a plurality of rings or ring members 33. As illustrated in FIG. 1, when the stent 1 is in an unexpanded state, each ring is positioned in a nested arrangement. For purposes of this application the term "nested" includes but is not limited to concentric, stacked, overlapping, and adjacent ring arrangements. The rings may surround a center point 31. As the stent 1 expands, at least one ring 33 is either self expanded or pushed by an expansion mechanism such as a balloon away from the ostium 38 and into the body vessel branch. The extension of the rings 33 forms a generally serial configuration and defines at least a portion of a generally tubular secondary fluid lumen 34 in fluid communication with the first fluid lumen 14. At least a portion of the secondary fluid lumen 34 is located between an ostial ring closest to the ostium 38 and an outermost ring 40. Some or all of the rings can be connected to each other by ring-ring connectors 37 or to the first stent body by ring-stent connectors 39. In one possible embodiment, each ring is connected to an adjacent ring by a connector 37 and only the ostial ring is connected to the first stent body by a connector 39.

Figure 3:
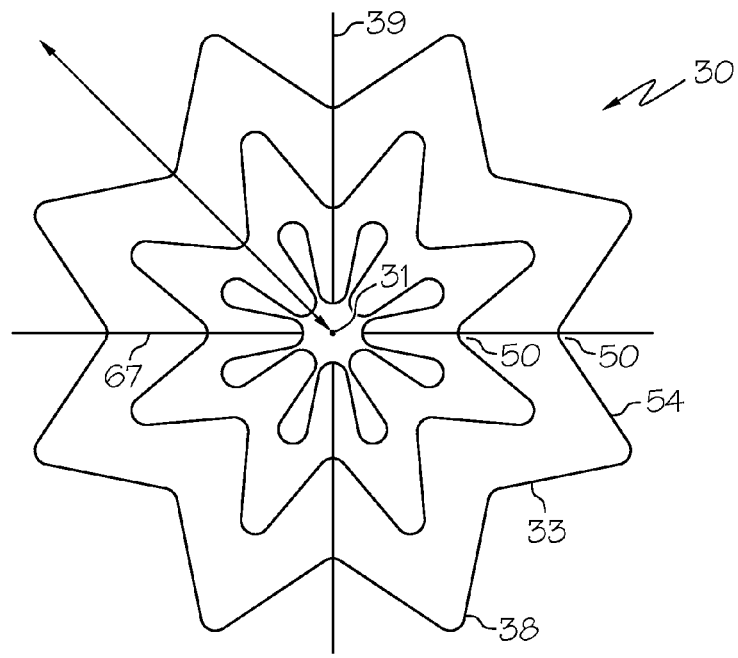
FIG. 3 is a view of a bifurcated stent with long bridges.

Referring now to FIG. 3 there is shown a detailed illustration of a side branch assembly designed according to the current state of the art. It features rings 33, connectors 67, and connectors 39. The rings are all in phase with each other and the inter ring connectors 67 can be characterized as connecting the peak 50 of one ring to the peak 50 of another. This design also features connectors 67 and connectors 39 extending into all of the rings and connecting with the first stent body 10.

For purposes of this application, the term "in phase" means the rings 33 are generally concentric and project towards and away from the center point 31 at relatively similar rotational positions along their perimeters. For example, peaks 50 of one ring 33 are aligned with peaks 50 of another ring 33 in a sidebranch radial direction In contrast, "out of phase" means the rings 33 are not in similar rotational positions. When rings are in phase, a connector 67 oriented along a vector generally directed towards the center point 31 is typically a peak-peak or valley-valley connection. Conversely, a connector 37 see FIG. 4) according to embodiments of the present invention connecting two out of phase rings can be a peak-valley connection. FIG. 3 features peak-peak connectors 67 and FIG. 4 features peak-valley connectors 37.

Figure 4:
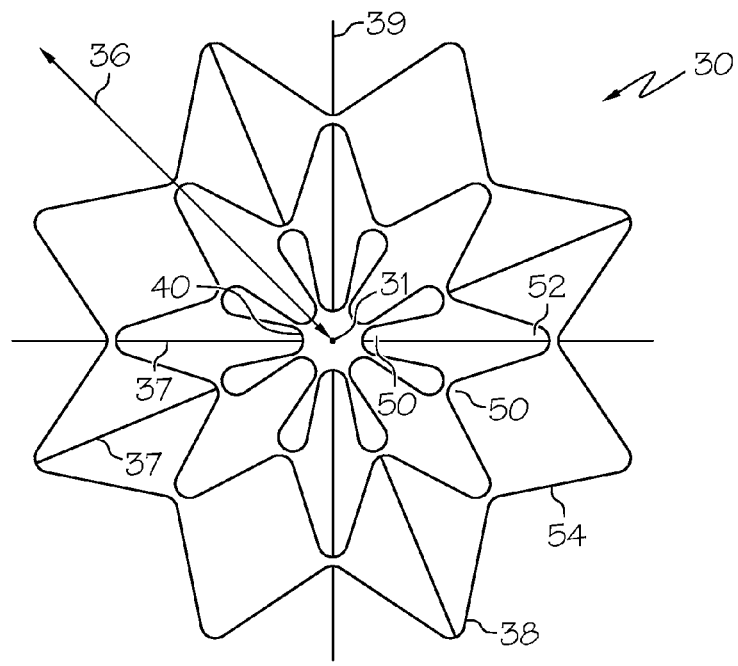
FIG. 4 is a detailed view of the side branch assembly of a bifurcated stent assembly made of rings connected by valley-valley bridges.

Referring now to FIG. 4 there is shown a detailed illustration of an embodiment for the improved side branch assembly 30. At least two of the rings 33 comprise a plurality of peaks 50 and valleys 52 connected by struts 54 extending along the rings' 33 perimeter. The rings 33 themselves are interconnected by at least one connector 37 connecting a peak 50 of one ring 33 to a valley 52 of an adjacent ring 33. By using peak-valley connectors 37 to link the rings 33, the extent of coverage the expanded side branch assembly provides to the body vessel increases. In addition, by replacing long connectors 67 of FIG. 3 with a multiplicity of shorter connectors 37 more widely distributed between different regions of the rings 33, the expanded side branch assembly 30 of FIG. 4 has greater flexibility than the side branch assembly of FIG. 3.

FIG. 4 is a representational illustration of the improved side branch assembly 30, but there are number of alternative designs that this invention encompasses. FIG. 4 contains three rings 33 a first and a third in phase with each other and a second exactly out of phase with the first and the third. The rings need not be exactly in phase with each other. In addition, the figure shows rings with eight peaks, eight valleys, four ring-ring connectors, and four ring-stent connectors and that every other valley is interconnected. Any number of connectors can be used. The figure also shows the connectors connecting a given ring to a less ostial ring are located on the valley immediately counterclockwise to a valley with an ostial connector or bridge. This relative positioning of the bridges and/or connectors is not an essential feature of the invention. This invention at a minimum encompasses a side branch assembly 30 with at least two rings each having at least two valleys, one connector and one bridge connecting the two valleys.

Although the figure shows a single side branch opening and a singe side branch assembly, there can be multiple side branch openings and side branch assemblies.

The sizes of the side branches can vary as well having larger, smaller or the same area, end-on-end length, or circumference in the extended or unextended states. Multiple side branch openings can be positioned anywhere along the length of the first stent body 1 and can be coaxially positioned relative to one another.

In embodiments wherein the side branch assembly 30 is configured to be self expanding, the stent 1 can be designed such that first body stent struts 5 can partially cover and restrain the side branch assembly 30 in the unexpanded state. In such an embodiment, as the first stent body 10 expands (whether through balloon expansion or by self expansion) its movement will move the covering struts 5 from the side branch assembly 30, allowing the side branch assembly to self-expand. In the case of a balloon expandable side branch assembly 30, the stent 1 can also be designed so that the unexpanded first stent struts 5 can at least partially cover the side branch assembly 30 and can be moved away as the first stent body 10 expands. As mentioned before, this inventive concept is not limited to stents comprising struts and can be accomplished with any stent structure in which in the unexpanded state the stent has a structural component adjacent to the structural components of the side branch assembly and in the expanded state the structural components are moved away from the side branch assembly.

One way to vary the degree of structural strength or flexibility that the expanded side branch assembly 30 will have is by constructing various parts of the side branch assembly 30 out of materials with different properties. For example, the connectors 39, connectors 37, and rings 33 can each be constructed out of different materials with differing structural strength or flexibility. In addition, each ring 33, each connector 37, or each connector 39, can be made out of similarly different materials.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, niobium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon or after being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising a tubular body having a sidewall with a plurality of openings therethrough, a portion of the sidewall having a plurality of rings which are concentric about a centerpoint located on said sidewall, including a first ring and a second ring, the first ring comprising alternating peaks and valleys connected by struts and the second ring comprising alternating peaks and valleys connected by struts, the peaks of a ring located closer to the centerpoint than the valleys of the ring, the first ring having the same number of peaks and valleys as the second ring, the struts of the second ring being longer than the struts of the first ring, and a connector extending from a peak of the first ring to a valley of the second ring, said connector being straight along its length.

2. The stent of claim 1 wherein the first and second rings are connected by a plurality of connectors, each connector extending from a peak of the first ring to a valley of the second ring.

3. The stent of claim 2 wherein each of the connectors extend in a side branch radial direction.

4. The stent of claim 1 further comprising a third ring concentric with said second ring, said third ring comprising alternating peaks and valleys connected by struts, the second ring having the same number of peaks and valleys as the third ring, the struts of the third ring being longer than the struts of the second ring, and a connector extending between a peak of the second ring and a valley of the third ring.

5. The stent of claim 4 wherein each peak of said first ring is aligned with a peak of said third ring in a side branch radial direction.

6. The stent of claim 4 wherein each valley of said second ring is aligned with a peak of said third ring in a side branch radial direction.

7. The stent of claim 1 wherein each peak of said first ring is aligned with a valley of said second ring in a side branch radial direction.

8. The stent of claim 1 in which at least one connector and at least one concentric ring are constructed out of different materials.

9. The stent of claim 1 wherein a connector is connected to every other peak of said first ring.

10. A bifurcated stent having a tubular sidewall, the sidewall including an expandable sidebranch portion, the expandable sidebranch portion comprising a plurality of rings which are concentric about a centerpoint, including a first ring and a second ring, the first ring comprising alternating peaks and valleys connected by struts and the second ring comprising alternating peaks and valleys connected by struts, the peaks of a ring located closer to the centerpoint than the valleys of the ring, the first ring having the same number of peaks and valleys as the second ring, each peak of the first ring aligned with a valley of the second ring in a sidebranch radial direction, the struts of the second ring being longer than the struts of the first ring, and a connector extending from a peak of the first ring to a valley of the second ring, said connector oriented in a sidebranch radial direction.

11. The bifurcated stent of claim 10 comprising a plurality of connectors, each connector extending from a peak of the first ring to a valley of the second ring.

12. The bifurcated stent of claim 10 in which the first ring defines the outermost end of the expandable sidebranch portion when the sidebranch portion is outwardly deployed.

13. The bifurcated stent of claim 10 in which each valley of the first ring is aligned with a peak of the second ring in a sidebranch radial direction.

14. The bifurcated stent of claim 10 in which at least one connector is more rigid than at least one ring.

15. The bifurcated stent of claim 10 in which at least one ring is more rigid than at least one connector.

16. The bifurcated stent of claim 10 in which at least one connector and at least one concentric ring are constructed out of different materials.

17. The bifurcated stent of claim 10 wherein a connector is connected to every other valley of said second ring.

18. A bifurcated stent being expandable from an unexpanded state to an expanded state, wherein in the unexpanded state the stent has a diameter less than that of the diameter in the expanded state, the bifurcated stent comprising:
 a substantially tubular primary body defining a sidewall, a primary lumen and having a primary longitudinal axis extending therethrough, said sidewall having a side opening;
 a side branch assembly engaged to the primary body and located within the side opening, the side branch assembly comprising at least two ring members, in the unexpanded state the at least two ring members being positioned substantially within the sidewall, in the expanded state at least one ring member being positioned external to the sidewall, and the at least two ring members defining a secondary lumen having a secondary longitudinal axis extending therethrough, the secondary lumen being in fluid communication with the primary lumen, the secondary longitudinal axis forming an angle with the primary longitudinal axis;

the ring members each comprising a plurality of alternating peaks and valleys connected by struts, the peaks of a ring located closer to a center of the side branch assembly than the valleys of the ring, the first ring having the same number of peaks and valleys as the second ring, the struts of the second ring being longer than the struts of the first ring, the ring members connected by at least one connector extending from a peak of one ring member to the valley of another ring member in a side branch radial direction.

19. The bifurcated stent of claim 18 comprising a plurality of connectors, each connector extending from a peak of the first ring member to a valley of the second ring member, wherein half of the valleys of the second ring member are connected to a connector.

* * * * *